United States Patent
Mead et al.

[11] Patent Number: 5,190,519
[45] Date of Patent: Mar. 2, 1993

[54] METHOD AND APPARATUS FOR PULSING WATER INTO THE COLON AREA

[75] Inventors: David P. Mead, Castle Rock; Thomas Shilling, Englewood; Ray Atchley, Golden, all of Colo.

[73] Assignee: Aegis Medical, Inc., Littleton, Colo.

[21] Appl. No.: 704,330

[22] Filed: May 23, 1991

Related U.S. Application Data

[63] Continuation-in-part of Ser. No. 247,734, Sep. 22, 1988, Pat. No. 5,019,056.

[51] Int. Cl.⁵ .............................................. A61M 1/00
[52] U.S. Cl. ...................................... 604/27; 604/39; 604/276
[58] Field of Search ............................... 604/27-35, 604/48, 54, 113-118, 131, 151, 150, 153, 257-264, 275-280; 600/29; 128/DIG. 12, 750; 251/5; 137/102, 844, 906

[56] References Cited

U.S. PATENT DOCUMENTS

| | | | |
|---|---|---|---|
| 2,257,072 | 9/1941 | Coombs | 604/35 |
| 4,637,814 | 1/1987 | Leiboff | 604/39 |
| 4,655,197 | 4/1987 | Atkinson | 604/30 |
| 4,682,979 | 7/1987 | Girouard | 604/48 |
| 4,874,363 | 10/1989 | Abell | 604/34 |

Primary Examiner—C. Fred Rosenbaum
Assistant Examiner—William W. Lewis
Attorney, Agent, or Firm—John E. Reilly

[57] ABSTRACT

A bowel care apparatus is characterized by having a pump circuit for pumping water under pressure through a speculum, and the pumping circuit may be placed in a pulse mode to further stimulate the rectal and colon areas during each infusion cycle.

10 Claims, 2 Drawing Sheets

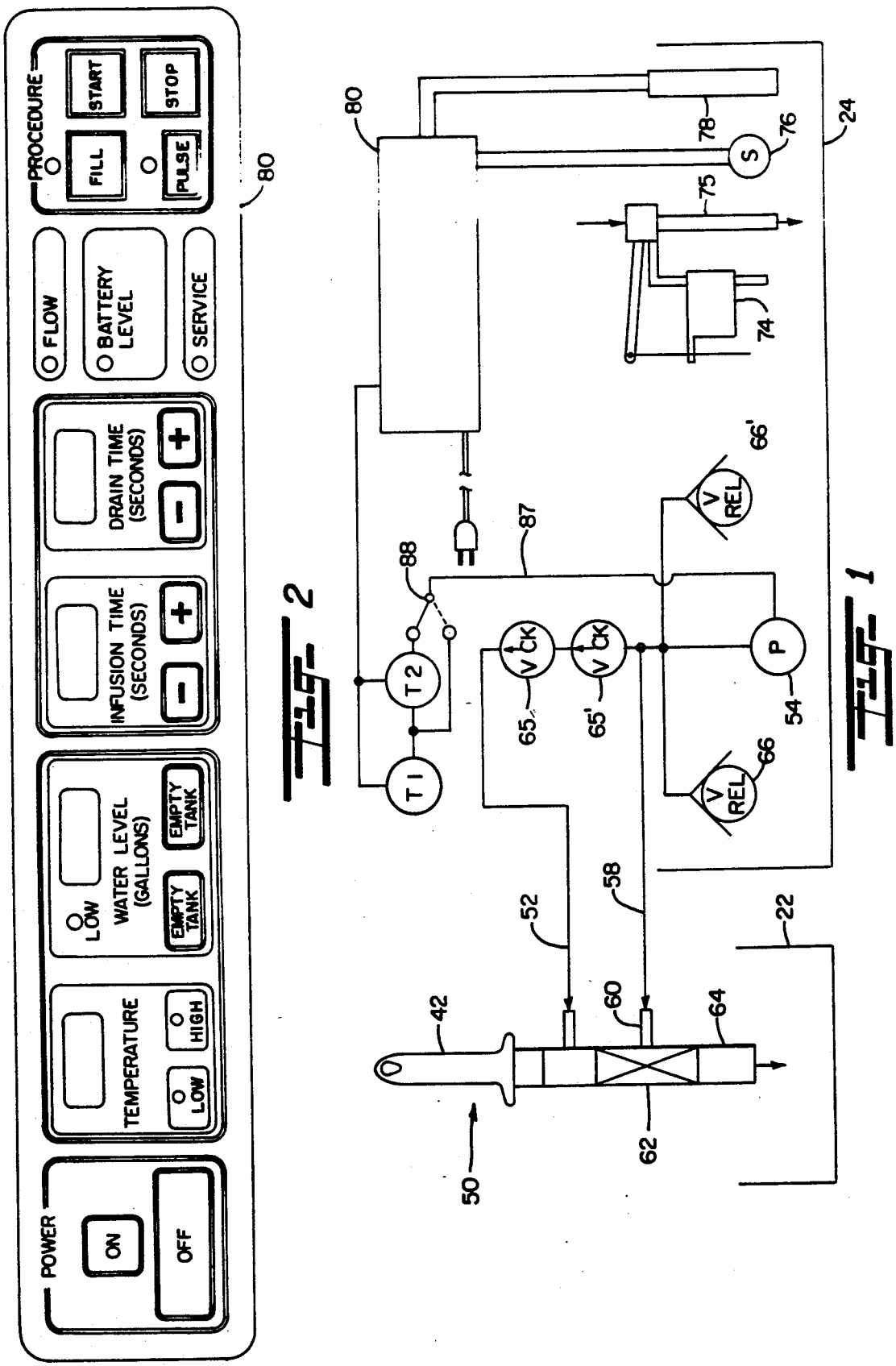

METHOD AND APPARATUS FOR PULSING WATER INTO THE COLON AREA

Reference to Cross-Related Applications

This application is continuation-in-part of Ser. No. 247,734, now U.S. Pat. No. 5,019,056 for BOWEL CARE APPARATUS, filed Sept. 22, 1988 by Alan R. Lee, David P. Mead, Robert A. Null, Thomas Shilling and Ray Atchley and assigned to the assignee of the present invention.

This invention relates to bowel care systems; and more particularly relates to a novel and improved method and apparatus for lavaging the colon.

BACKGROUND AND FIELD OF THE INVENTION

Various types of systems have been devised for irrigating and lavaging the colon for the purpose of dislodging waste or fecal material and are particularly beneficial for elderly and handicapped patients. In such systems, it is desirable that the mechanism employed be compact, sanitary and easy to use and readily conformable to meet the particular requirements and physical condition of the patient.

Typically, systems which have been employed for colonic lavage have a nozzle or speculum which is inserted into the rectum and water is directed from a tank or reservoir at a predetermined temperature and pressure level through the speculum into the colon of the patient. After a predetermined time interval, the liquid and waste material are withdrawn from the patient via the speculum and through a waste or drain line into a waste container. The flow of water into the patient is regulated to some extent by closing the drain line and, once the colon is filled to a predetermined level, the drain line is opened so that the water and waste material are then free to flow back through the nozzle and drain line into the waste container. In this relation, it has been proposed to control the opening and closing of the drain line by means of a valve which is either pressure or manually operated to open and close that line either according to a particular pressure level or time interval.

In colonic lavage systems it is desirable to minimize the amount of water required in conducting a complete lavaging operation but at the same time to greatly enhance the ability of the system to erode or break up fecal material in the colon and to facilitate its removal in a dependable and highly efficient manner.

SUMMARY OF THE INVENTION

Accordingly, it is an object of the present invention to provide for a novel and improved bowel care system which employs a minimum number of parts, is highly efficient and dependable in use while conserving on the amount of water required to perform a complete colonic lavaging operation.

It is another object of the present invention to provide for a novel and improved method and apparatus for colonic lavage in which closely coordinated fill and drain sequences may be performed automatically or under the control of the patient in alternating cycles of operation and in a closely coordinated sequence of steps in which the duration of filling and draining may be regulated to assure maximum effectiveness and relief to the patient.

An additional object of the present invention is to provide in a colonic lavage apparatus for a novel and improved method and means for removing colon impactions, and more particularly wherein water can be pulsed at the desired frequency or rate to most effectively break up fecal material in the colon with a minimum of discomfiture to the patient.

In accordance with the present invention, a novel and improved form of pumping circuit has been devised for use in a colonic lavage system of the type in which a speculum is insertable into the rectum of a patient, a liquid fill line is provided for delivering liquid under pressure through the speculum into the patient's colon from a liquid supply source, and the improved pumping circuit comprising pump means for pumping liquid under pressure from the source through the speculum into the colon, timer means for sequentially activating and deactivating the pump means over predetermined time intervals whereby to deliver liquid under pressure over a predetermined time interval, and pulse means for delivering pulses of liquid through the speculum at closely spaced time intervals within each said first predetermined time interval.

In the pumping circuit, preferably a pumping unit is controlled by a first timer to be activated over a predetermined time interval to establish the infusion or fill cycle during which water is delivered under pressure to the patient, and at the end of that fill cycle, the pump is deactivated to permit the water and any waste material to be drained from the patient. During the fill cycle, water can be delivered in pulses by means of a second timer which rapidly starts and stops the pump at the desired frequency or rate to most effectively break up the fecal material in the colon. Alternate forms of pumping circuits are provided in which an auxiliary pump is provided either to deliver pulses of water in an additive or subtractive/additive mode to the patient.

Other objects, advantages and features of the present invention will become more readily appreciated and understood when taken together with the following detailed description in conjunction with the accompanying drawings, in which:

BRIEF DESCRIPTION OF THE DRAWINGS

FIG. 1 is a diagrammatic view of a pumping circuit in accordance with the present invention;

FIG. 2 is a front view in elevation of a control panel employed in connection with the pumping circuit shown in FIGS. 1, 3 and 4;

DETAILED DESCRIPTION OF THE PREFERRED EMBODIMENTS

Figure 3:
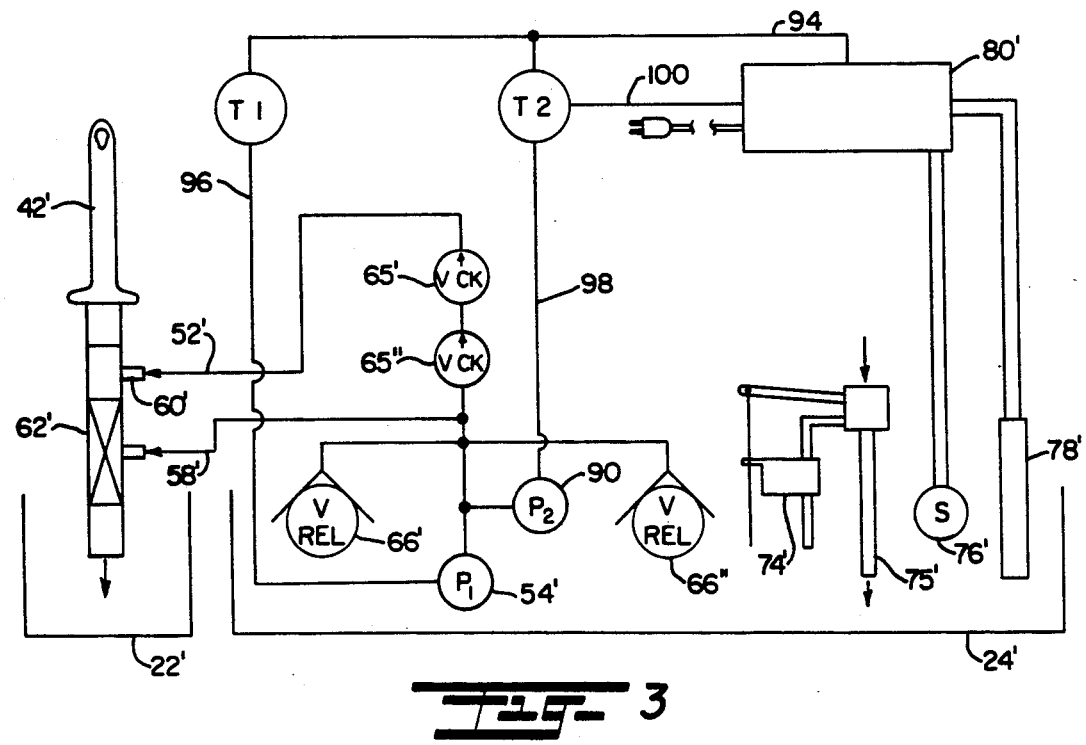
FIG. 3 is diagrammatic view of another form of pumping circuit in accordance with the present invention.

Referring in more detail to the drawings, a colonic lavage apparatus in accordance with the present invention is shown in FIG. 1 and broadly comprises a pump circuit 50 mounted within the interior of a receptacle 24, the circuit including a supply tube 52 extending from the outlet of the pump 54 for connection to the speculum 42. In addition, a small diameter valve control tube 58 extends from the tube 52 at the outlet side of the pump into a pressure port 60 in a sidewall of a control or sphincter valve 62 which is connected in close proximity to the speculum, and a drain line extends into the waste reservoir 22. The pump circuit 50 includes two check valves 65, 65' in series to prevent return or backflow of fluid from the speculum 42; and a pair of pressure relief valves 66, 66' are connected into fill line 52 ahead of the check valves, the pressure relief valves 66, 66' being designed to open in response to liquid pressure in the water fill line 52 in excess of a predetermined level, such as, on the order of 2 psi. The pressure relief valves 66, 66' are spring-loaded valves which in a well-known manner are normally closed when the water pressure is below the predetermined level. For example, if the maximum pressure is established at 2 psi, the spring pressure is such that the valve will not open until the 2 psi level is reached and, when the water pressure exceeds that level, one of the valves will open to bypass some of the water back into the container 24. In this relation, some redundancy is built into the system so that if one of the valves 66, 66' should fail the other will be operative to open at the preset pressure level in order to avoid excess pressure in the fill line.

Similarly, a pair of check valves 65 and 65' are provided so that in the event that one should fail the other is operative to prevent backflow of water through the fill line 52.

The valve control tube 58 is a relatively small diameter tube in relation to the fill line 52 and supplies a small quantity of fluid under pressure from the outlet side of the pump 54 into the valve pressure port 60. The valve 62 operates on the principle of remaining in an open position as long as the pressure inside of the control valve 62 exceeds that delivered through the pressure port 60. Conversely, the valve will close when the pressure in the valve tube 58 exceeds that of the water pressure in the speculum or valve interior. Design of the valve permits it to be highly sensitive to differential pressures and, for example, requires a difference of less than $\frac{1}{4}$ psi between the colonic pressure and pressure in the valve tube to close.

As further shown in FIG. 1, a standard float valve 74 is mounted in direct association with inlet tube 75 to sense the water level in the receptacle 24 and to interrupt the flow of water supply when it reaches a predetermined level, for example, 5 gallons. A suitable form of float valve 74 is a Fluidmaster Model 702, manufactured and sold by Fluidmaster, Inc. of Anaheim, Calif. In addition, a float switch 76 is positioned at the lower end of the reservoir 24 and senses a low water condition in the reservoir 24 to turn off the pump 54. One commercially available switch is a Model 504 float switch, manufactured and sold by Revere Corporation of America, Wallingford, Conn. The pump 54 may be a Supersub 88 electric pump manufactured and sold by Munster Simms Engineering, Ltd. of Bangor, Northern Ireland.

A conventional form of temperature sensor or probe as represented at 78 is provided to sense the temperature in receptacle 24, such as, a Model 8D590LH, manufactured and sold by Analog Devices of Norwood, Mass.

In the pump circuit 50, when the pump 54 is activated, water is discharged under pressure through the water fill line 52 and the speculum 42. Water is simultaneously directed under pressure from the pump via pressure tube 58 to the valve 62 and, so long as the water is flowing freely into the colon, the water pressure in the pressure tube 58 will exceed that in the speculum or colon thereby causing the valve 62 to close. If the flow into the colon should exceed the capacity of the colon, this condition will be detected by a rapid increase in pressure of the water in the fill line 52 and once the pressure reaches the maximum pressure level of the pressure relief valves, such as, 2 psi will cause one of the valves 66, 66' to open and return water into the supply receptacle.

At the end of a fill cycle, the pump 54 is deactivated to discontinue flow of water into the fill line 52, and the sphincter valve 62 will then open as a result of the greater pressure of the return flow of water from the patient via the speculum into the interior of the valve 62 and the absence of pressure in the pressure tube 58. The fluid contents of the colon are thereby allowed to be removed through the drain line 64 into the waste reservoir 22. The drain sequence will continue for a predetermined time interval necessary for removal of the liquid and waste and as aided by the peristaltic action of the patient. The fill and drain cycles are then repeated until the patient terminates the treatment or an alarm condition should turn the unit off.

An important feature of the pump circuit illustrated in FIG. 1 resides in first and second timer circuits $T_1$ and $T_2$ which are connected in series with the pumping unit 54 via electrical control line 87, and a pulse mode switch 88 is positioned in the control line 87. The timer circuit $T_1$ has a separate control line 89, the pulse mode switch being a two-position switch that can be advanced between a first position establishing contact with the control line 89 from the timer $T_1$ and a second position establishing contact with the control line from the timer circuit $T_2$. Each of the timer circuits T1 and T2 may be a time delay relay, such as, the Model 90F7642 Type CNT-35-26 manufactured and sold by Potter & Brumfield of Princeton, Ind. The timer $T_1$ is preset with a time duration of anywhere from 1 second to 29 seconds to establish the fill or infusion time, and the timer circuit $T_2$ will switch the pump 54 on and off automatically during each infusion cycle. The pulsing rate may be set to intermittently start and stop the pump 54 as rapidly as twenty times per second so that the water discharged from the pumping unit 54 will be rapidly pulsed via the fill line 52 and speculum 42 into the colon.

In carrying out a typical operation, the fill reservoir 24 has a fitting or port, not shown, for connection of a hose from a source of tap water, such as, the standard plumbing system in a building to deliver hot and cold water via the inlet tube 75 into the receptacle 24, and the temperature of the water is controlled to be in the range of 92° F. to 104° F. Otherwise, if the water in the reservoir 24 is outside the requisite temperature level, the system is not operable and the temperature light on the panel 80 will be activated. For instance, the machine may be filled to a 5-gallon level in reservoir 24, and the float valve 74 is activated when filled to that point to prevent any more water from being introduced into the reservoir 24.

The optimum fill/drain sequence is determined by trial and error for a given patient and specifically to determine the time duration necessary to fill the colon cavity with water. Typically, for a pump operating at a capacity on the order of 2 gallons per minute, the duration of fill may be on the order of 5 to 12 seconds at a pressure level of less than 2 psi. For most effective use, the patient is placed in a prone position and at a level above the waste reservoir 22. A speculum 42 is inserted through the anal canal and into the rectum. When a fill sequence is initiated in the manner described, the pump 54 is activated to pump water through the fill line 52. If at any time during the fill sequence the pressure should increase to the maximum 2 psi level, one of the pressure relief valves 66, 66' will be caused to open so that the water is bypassed directly back into the reservoir.

At the end of the fill interval, the pump is turned off, as a result of which the pressure in the valve control line 58 is removed and the pressure or head of water is sufficient to open the valve 62 for the purpose of draining downwardly through the drain line 64 into the waste reservoir 22. Either one of the check valves 65, 65' will prevent return flow of the liquid and waste matter through the fill line 52. During the fill sequence, the differential pressure between the fill line 52 and valve control line 58 is on the order of ¼ psi and in this way the greater pressure in the valve control line 58 will cause the liner valve 62 to remain closed during the fill operation. Of course, any patient-induced pressure during the fill cycle which would cause the return pressure in the speculum acting against the interior of the valve liner 73 to be greater than that in the control tube 58 would cause the valve 62 to open temporarily during the fill cycle to relieve or reduce that pressure in the colon.

Removal of water and waste material during the drain sequence is aided by any peristaltic action of the patient, and the duration of that sequence will be governed greatly by the ability of the patient to assist in draining or removal of waste. Typically, the fill/drain sequence is repeated over a number of cycles and may, for example, require a total time duration of 15 to 20 minutes either until the water supply is depleted in the reservoir or the patient or attendant can see that the water is clear and no further waste material has to be removed. Here, the float switch 76 in the reservoir 24 will signal a low water condition and automatically turn off the pump 54 as well as light the display light on the panel.

A front panel layout 80' is illustrated in FIG. 2 and includes a "POWER" panel section with "ON" and "OFF"; a temperature control section including "LOW" and "HIGH" light displays as well as a temperature display; a water level section having a "LOW" light display to indicate a low water level condition; a pair of "EMPTY TANK" buttons which must be depressed simultaneously to drain the tank or reservoir; "INFUSION TIME" and "DRAIN TIME", displayed in seconds, are selected by depressing either of the "PLUS" or "MINUS" buttons for each segment of the cycle. These control buttons may actually form part of the timed delay circuit $T_1$, and the time interval may be selected basically over a range of 1 second to 29 seconds and typically may be selected to provide 5 to 6 seconds fill time and 12 to 15 seconds drain time, although this will vary from patient to patient. Suitable light displays are provided to indicate water flow, battery level and when the system requires servicing. Finally, a procedure section is provided with control buttons to regulate "FILL", "START", "STOP", and "PULSE". The "START" button will initiate the fill cycle, assuming that "POWER" is "ON"; and the "STOP" button will interrupt the fill cycle when manually depressed. In this relation, a limited degree of pulsing or vibration may be generated by turning the pumping unit 54 on and off with great rapidity and specifically by toggling or depressing the "START" and "STOP" buttons on the control panel during the fill cycle. When manually activated in this manner, the "START" and "STOP" buttons will effectively override the normal infusion time selected on the panel. The "PULSE" button forms a unitary part of the timer circuit $T_2$ and will, when depressed, cause the pump to be pulsed at a greatly increased rate during the fill cycle thereby increasing the mechanical activity of the water and give the sensation that the water is being vibrated. The motion of the water when pulsed is to the end of providing increased stimulation to the nervation of the rectum and colon so as to induce both peristaltic activity as well as defecation which may not otherwise take place. Another benefit of the pulse mode is to enable the water to erode or break up fecal material in the colon thus allowing the therapeutic activity of removing colon impactions.

In FIG. 3, like parts are correspondingly enumerated to those of FIG. 1 and employs a control panel 80' corresponding to the control panel 80 of FIG. 2 as well as timer control circuits $T_1$ and $T_2$. An alternate form of pumping circuit 50' includes a supply tube 52' extending from the outlet of pump 54' for connection to speculum 42'. The small diameter valve control tube 58' extends from the outlet side of the pump 54' in the pressure port 60' of the control valve 62' and drain line 64' extends into a waste reservoir 22' The two check valves 65" are connected in series to prevent backflow of liquid from the speculum 42", and the pressure relief valve 66" will open in response to liquid pressure in the line 52' in excess of a predetermined pressure level. Again, if the maximum pressure is established at 2 psi, the spring pressure is such that the valve 62' will not open until that level is reached whereupon one of the relief valves 66" will open to bypass water back into the main reservoir or container 24'.

The valve 62' remains in an open position as long as the pressure inside of the valve exceeds that delivered through the pressure port 60' but will close when the pressure in the tube 58' exceeds that of the water pressure in the speculum 42' or valve interior. The standard float valve 74' associated with inlet tube 75' senses the water level in the receptacle or reservoir 24' to interrupt the flow of water into the receptacle when it reaches a predetermined level as indicated on the front control panel. The temperature probe 78' senses the temperature level of the water in the reservoir 24'. An auxiliary pumping unit 90 draws water through its intake side from the reservoir 24, and its discharge side is connected via line 92 to the discharge side of the pump 54' and specifically connected into the fill line 52' from the pump 54'. The timer circuits $T_1$ and $T_2$ are independently connected to the electrical supply line 94 from the control panel 80'. The timer circuit $T_1$ is in turn connected via electrical line 96 to the pump 54', and the timer circuit $T_2$ is connected via line 98 to the auxiliary pumping unit 90. If the "PULSE" button on the panel is not depressed, the timer circuit $T_1$ will operate as described in connection with FIG. 1 to provide a steady state DC signal directly to the pump 54' during each infusion cycle. Briefly, this infusion cycle is determined by selecting the time intervals at the "INFUSION TIME" and "DRAIN TIME" panel sections as described.

If the "PULSE" button is depressed to activate the timer $T_2$ via control line 100, the pump 90 is switched on and off automatically during each infusion cycle thereby adding the pulsed output of the pump 90 to the fill line 52'. The pump unit 54' remains on during this pulse mode so that the pulsed water discharged by the pump 90 is added to the discharge of the pump 54'.

Preferably, the pump 90 is a March submersible 12 VDC pump and is a centrifugal pump, although a reciprocating piston pump could be used in place of the centrifugal pump. The effect of the additive pulsed water flow or energy is to create an induced pressure wave or vibration of the water directed into the rectal and colon areas during the infusion or fill portion of each cycle and typically would be established at an extremely high rate, for example, on the order of 10 pulses per second.

Figure 4:
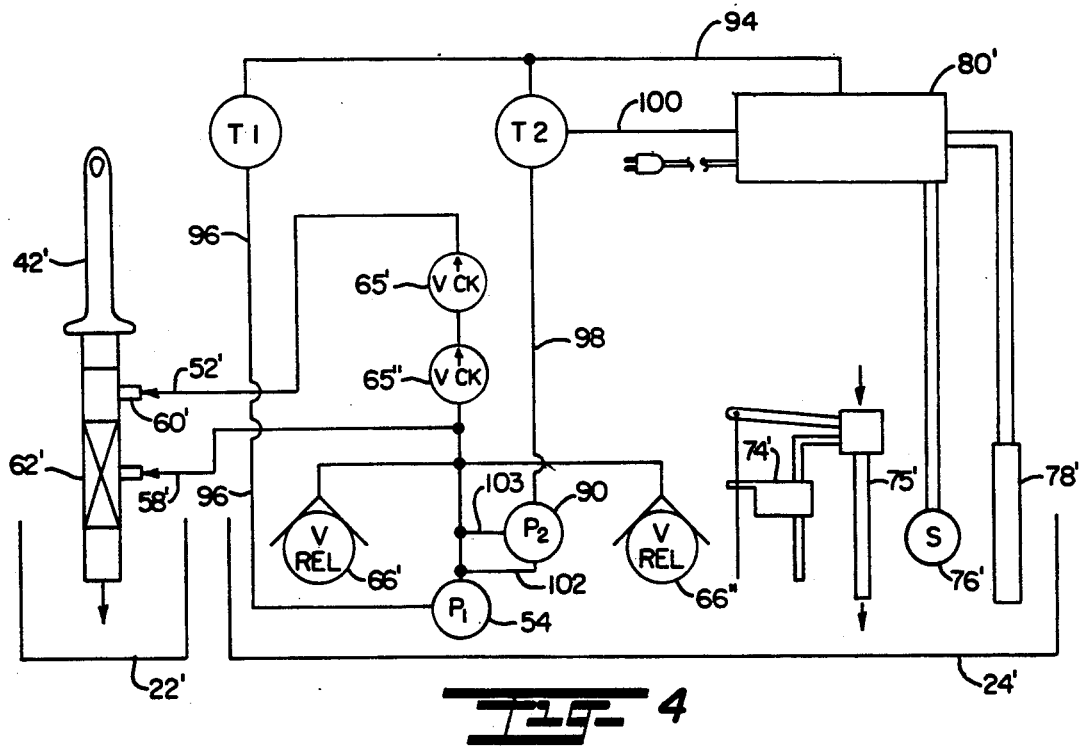
FIG. 4 is a diagrammatic view of still another modified form of pumping circuit in accordance with the present invention.

Still another form of pumping circuit is illustrated in FIG. 4 in which the auxiliary pumping unit 90 has intake and return lines 102 and 103 both connected to the discharge side of the pump 54' or in the fill line 52'. The balance of the pumping circuit is not illustrated, since it corresponds to that shown in FIG. 3. Similarly, the timing circuits $T_1$ and $T_2$ correspond to that of FIG. 3 so that if the pulse mode is off the timer $T_1$ provides steady DC voltage to the pump 54' during each infusion cycle. When the pulse mode PM is depressed, the timer $T_2$ will then activate pump 90 so that a portion of the water from the pump 54' is bypassed into the pump 90, then is reintroduced in pulsed stages into the fill line so as to create more of a subtractive/additive mode in pulsing or vibrating the water through the fill line during the infusion cycle, especially should a reciprocating piston pump be employed.

It is therefore to be understood from the foregoing that various modifications and changes may be made in the construction and arrangement of elements comprising the preferred embodiment of the invention as described herein without departing from the spirit and scope of the present invention as defined by the appended claims.

We claim:

1. In colonic lavage apparatus wherein a speculum is insertable into the rectum of a patient, a liquid fill line is provided for delivering liquid under pressure through said speculum into the patient's colon from a liquid supply source, the improvement comprising:
    pump means for pumping liquid under pressure from said source through said speculum into the colon;
    first timer means for sequentially activating and deactivating said pump means over first and second predetermined time intervals, respectively, whereby to deliver liquid under pressure over said first predetermined time interval; and
    pulse means associated with said pump means including second timer means for delivering pulses of liquid through said speculum at closely spaced time intervals within each said first predetermined time interval.

2. In apparatus according to claim 1, said pulse means including an auxiliary pump having an intake port in communication with said source and a discharge port in communication with said fill line between said pump means and said speculum.

3. In apparatus according to claim 2, said pulse means including auxiliary timer means for said auxiliary pump for sequentially activating and deactivating said auxiliary pump means over closely spaced time intervals within each of said predetermined time intervals.

4. In a colonic lavage apparatus wherein a speculum is insertable into the rectum of a patient, a liquid fill line is provided for delivering liquid under pressure through the speculum into the patient's colon from a liquid supply source, and a drain line is provided for draining liquid and waste material from the patient's colon, the improvement comprising:
    pump means for pumping liquid under pressure from said source through said speculum into the colon;
    first timer means for sequentially activating and deactivating said pump means over first and second predetermined time intervals whereby to deliver liquid under pressure over said first predetermined time interval when said pump means is activated; and
    second timer means for sequentially activating and deactivating said pump means at closely spaced time intervals within each said first predetermined time interval whereby to deliver pulses of liquid through said speculum during each said first predetermined time interval.

5. In apparatus according to claim 4, said pump means including first and second units, said second timer means associated with said second pumping unit to sequentially activate said second pumping unit at said closely spaced time intervals.

6. In apparatus according to claim 5, said second pumping unit communicating with said fill line from said first pumping unit.

7. In apparatus according to claim 5, said second pumping unit having an intake and discharge port both in communication with said fill line from said first pumping unit.

8. In apparatus according to claim 4, said first and second timer means including manually operable control switches.

9. In colonic lavage apparatus wherein a speculum is insertable into the rectum of a patient, a liquid fill line is provided for delivering liquid under pressure through said speculum into the patient's colon from a liquid supply source, the improvement comprising:
    pump means for pumping liquid under pressure from said source through said speculum into the colon;
    timer means for sequentially activating and deactivating said pump means over first and second predetermined time intervals whereby to deliver liquid under pressure over said first predetermined time interval; and
    pulse means including an auxiliary pump connected to said fill line between said pump means and said pump means and said speculum for delivering pulses of liquid through said speculum at closely spaced time intervals within each said first predetermined time interval.

10. In apparatus according to claim 9, said pulse means including an intake port and discharge port, said intake and discharge port being in communication with said fill line between said pump means and said speculum, and auxiliary timer means for sequentially activating and deactivating said auxiliary pump at closely spaced time intervals within each of said predetermined time intervals.

* * * * *